United States Patent [19]

Weeks

[11] Plant 4,357

[45] Dec. 26, 1978

[54] ROSE PLANT

[76] Inventor: O. L. Weeks, 926 W. Philadelphia St., Ontario, Calif. 91761

[21] Appl. No.: 837,746

[22] Filed: Sep. 29, 1977

[51] Int. Cl.[2] ..... A01H 5/00
[52] U.S. Cl. ..... Plt./18
[58] Field of Search ..... Plt./17-19

*Primary Examiner*—Robert E. Bagwill
*Attorney, Agent, or Firm*—Frank B. Robb

[57] ABSTRACT

There is disclosed a new variety of rose of the hybrid tea class whose parentage is not known, having a distinct and unusual blending of corals in blooms ranging from bright coral when first opened to smooth, soft, champagne color when full blown, that color being retained for days while on the plant, the flowers being heavily petaled, open, and of distinct rose perfume, good hybrid tea habit, with strong straight stems for cutting and abundance of blooms.

1 Drawing Figure

The present invention relates to a new and distinct variety of rose plant of the hybrid tea class, which I identify as 75-R-03 which is the result of growing a seed placed with other seeds from other populations, and is what is known in the trade as a "floater", these various seeds being all planted together to observe what might happen during growth. Many of these seeds grow although unidentified as to exact parentage and the rose of the instant variety is such a product.

In view of the characteristics which it did display, it was selected to grow as a seedling, and as a result of growth and reproduction, provides a new and immproved rose variety distinguished from other hybrid tea roses as well as all other roses, and rose varieties of which I am aware, as evidenced by the following unique combination of principal characteristics which are outstanding in the new variety:

(1) Heavily petaled flower of open form;

(2) Distinct rose fragrance;

(3) Unusual color blending of corals ranging from moderate bright coral when flower first opens changing to smooth mellow, soft, champagne coral when full blown;

(4) Excellent hybrid tea habit with strong straight stems for cutting; and (5) Attractive blooms produced in abundance.

Inasmuch as the parentage is not known, it is not possible to make direct comparison with such parent, it is however clear to me that my new variety is definitely a hybrid tea rose.

Although this rose was originally grown from seed as setforth hereinbefore, successive generations grown from budding to determine asexual reproduction characteristics, clearly disclose that the aforementioned characteristics and distinctions come true to form and are transmitted in such asexual reproduction performed by me through generations produced thereby.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Munsell's Color Cascade, published by Macbeth Division of Kollmorgen Corp. of Baltimore, Md., except where general color terms of ordinary dictionary significance are appropriate:

Type: Hardy; tall; bush; outdoor; seedling; for cut flowers and for garden decoration.

Class: Hybrid tea.

Breeding: Seedling.

*Seed parent.*—Unknown.

*Pollen parent.*—Unknown.

Propagation: Holds its distinguishing characteristics through successive propagations by budding.

FLOWERS

Locality where grown and observed: Ontario, Calif.

Flowers borne: Singly, and 2 or 3 to stem; in semi-irregular, branching arrangement on strong long stems generally in rounded clusters.

Quantity of bloom: Free and abundant, both outdoors and in the greenhouse.

Continuity: From intermittent to continuous.

Fragrance: Penetrating, strong and spicey.

Bud:

*Peduncle.*—Medium to long; erect; dull green with some reddishness; entirely smooth.

*Before calyx breaks.*—Size — Medium to small. Form — Medium length; pointed; with conspicuous neck; with foliaceous appendages on the surface of the bud; the foliaceous parts extending beyond the tip of the bud equal to ½ to ¾ or more of its length. Color — Not significant.

*As calyx breaks.*—Color — Medium dull pink but relatively insignificant.

*As petals first open.*—Size — Small to medium. Form — Long and ovoid. Color — Outside — Essentially light pink with yellow shading at base. Inside — A blend of pink and peach.

*Opening.*—Opens up well.

Bloom:

*Size (when fully open).*—Medium to large, from 3 to 5 inches.

*Petalage.*—Very double (many petals, usually 40 to 50 petals).

*Form.*—Very ovoid at first, becoming high centered; petals being at first very tightly cupped, rolled inward, becoming later at maturity very tightly cupped and rolled outward.

Petals:

*Texture.*—Moderately thick, satiny with outside somewhat shiny.

*Shape.*—Outside — Round to oval; slightly scalloped; with apex flat with 2 to 3 notches. Intermediate — Round; slightly scalloped with apex flat with 1 notch. Inside — Round; slightly scalloped with apex flat with 1 notch.

This descriptin of a newly opened flower was made from a rose grown outdoors in the month of September at Ontario, Calif.

*Color.*—Outside petal — Outside surface — Yellow green segment at the base 23-7 blending upward into a light yellow green 23-4 with a further blending of light pink 40-2, blending upward into a medium pink between 39-4 to 40-6 with the top edge a darker pink 40-6. Inside surface—Bottom segment a deep gold 26-6 blending up to a pale yellow 26-3 continuing into a pale pink 40-2 with further blending at the top center of petal into a dark vermillion 42-8. Intermediate petal — Outside surface — Lower segment, light yellow green 24-3 blending up into a reddish pink 38-6 with a yellow green streak 24-3 extending ¾ of the way to the tip of the petal, ending with a light pink at the apex 38-1. Inside surface — Deep yellow gold 26-6 blending up into a pale yellow 23-3, continuing into a light yellow pink 36-3 with upper part of petal veined with a medium pinkish orange 36-6. Inner petal — Outside surface — A dark golden yellow 26-6, blending into a light yellow 26-3, continuing upward into a medium light pinkish orange 36-5. Inside surface — Base segment medium yellow green 25-7, blending up and out to a pale yellow 25-3 with a streak up the center of the petal a whitish yellow 25-2, with overall petal a dark pink 39-7.

The following description was made of a rose that was opened for three days outdoors during the month of September at Ontario, Calif.:

*Color.*—Outer petal — Outside surface — Bottom segment, medium dark golden yellow 26-6, blending to a light yellow 26-4, continuing upward into shades of medium pink 40-4, ending in shades of dark pink 40-8. Inside surface — Lower portion a medium yellow gold 26-6 blending up into a light yellow 26-4 continuing into a light pink 40-2 blending further upward into an overall pale pink of 36-1. Inside petal — Outside surface — Bottom segment a medium yellow gold 26-6, with a green yellow streak 26-4, continuing from the base to the top of the petal with the remainder of the petal a pastel pinkish orange 35-4. Inside surface — Bottom segment a medium yellow gold 28-6, blending into a light yellow 27-4 with large remainder of petal a pale pink of essentially a 36-1 with portions a light pink 36-2.

*General color effect.*—Newly opened flower — Primarily a light pink with a hint of orange combining a 36-4, 36-3 and 36-2. 3-days open — Primarily a medium pink orange 36-3 blending with 36-2 and ending with a pale pink 36-1. Behavior — Drop off cleanly. Flower longevity — On bush in garden — 4 to 5 days in September. Cut roses grown outdoors and kept at living room temperatures — 4 to 5 days in September.

REPRODUCTIVE ORGANS

Stamens: Medium number; arranged regularly about pistils, mixed with petaloids; tucked in calyx.

Filaments: Medium, many; without anthers.

Anthers: Medium; yellow to reddish; all open at various times.

Pollen: Moderate to abundant.

*Color.*—Gold yellow.

Pistils: Medium to many.

Styles: Short to medium length; thin caliper; very bunched.

Stigma: White.

Ovaries: All enclosed in calyx.

Hips: None observed.

Sepals: Permanent; moderate to long; curled.

*Color.*—Light green blending to slight reddish brown.

Seeds: None observed.

PLANT

Foliage:

*Leaves.*—Compound 5–7 leaflets; moderately abundant; medium to large size; somewhat heavy and leathery.

*Leaflets.*—Shape — Ovate, with apex obtuse to acuminate; base round to obtuse; margin-irregularly serrate.

*Color.*—Mature — Upper surface — Medium to dark green. Under surface — Moderately gray, green, with some light reddish veins. Young — Upper surface — Moderately reddish bronze. Under surface — Light to normal reddish bronze.

*Rachis (the supporting stem of the compound leaf).*—Light to medium weight. Upper side — Smooth; grooved. Under side — Moderately smooth.

*Stipules.*—Moderately to short length; moderately narrow width; moderately short points, turning out at an angle of less than 45° to 90°, recurved toward the stem.

This cultivar has about average to medium susceptibility to the usual rose insects and diseases.

Growth:

*Habit.*—Tall; bushy; upright; branched.

*Growth.*—Vigorous.

*Canes.*—Light to medium caliper.

*Main stems.*—Color — Dull green. Large prickles — Few to several; short almost straight; short oval base. Color — Light gray. Small prickles — None. Hairs — None.

*Branches.*—Color — Dull, yellowish green. Large prickles — Few to several; short to medium length; hooked downard; narrow base. Color — Yellowish green. Small prickles — None to few. Color — Brown. Hairs — None.

*New shoots.*—Color — Dull bronze. Large prickles — Medium to long; essentially straight slightly hooked downward; narrow base. Color — Bronze with some green blend. Small prickles — Few. Color — Brownish yellow. Hairs — None.

I claim:

1. A new and distinct variety of rose plant of the hybrid tea class, substantially as herein shown and described, characterized particularly as to novelty by the distinct and unusual color of its blooms primarily a medium pink orange, 36-3 blending with 36-2 and ending with a pale pink 36-1 when full blown, the long lastingness of the bloom color on the plant, heavily petaled, open flower form, distinct rose perfume, good tea habit with strong straight stems, the blooms being produced in abundance for cutting.

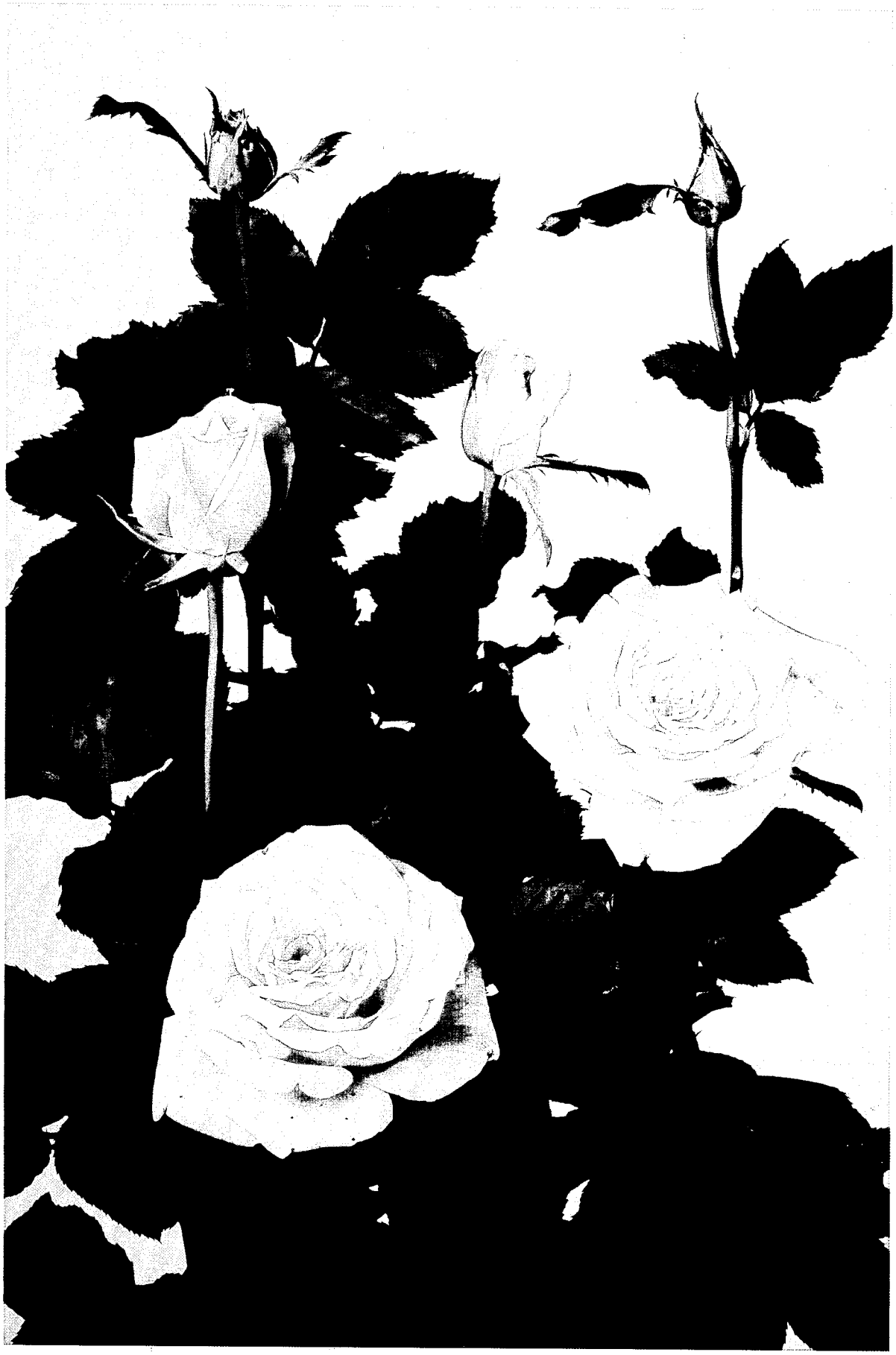

* * * * *